United States Patent [19]

Stanley et al.

[11] Patent Number: 5,446,155
[45] Date of Patent: Aug. 29, 1995

[54] METHOD FOR PREPARING DISUBSTITUTED MONOCHLOROTRIAZINES

[75] Inventors: Thomas J. Stanley; Sterling B. Brown, both of Schenectady; Paul E. Howson, Latham, all of N.Y.

[73] Assignee: General Electric Company, Schenectady, N.Y.

[21] Appl. No.: 298,084

[22] Filed: Aug. 30, 1994

Related U.S. Application Data

[63] Continuation of Ser. No. 117,384, Sep. 7, 1993, which is a continuation of Ser. No. 957,111, Oct. 7, 1992, abandoned.

[51] Int. Cl.$^6$ ............................................. C07D 251/26
[52] U.S. Cl. .................................... 544/218; 544/216; 544/219
[58] Field of Search ...................... 544/216, 218, 219

[56] References Cited

U.S. PATENT DOCUMENTS

| | | | |
|---|---|---|---|
| 4,895,945 | 1/1990 | Brown et al. | 544/218 |
| 5,089,044 | 2/1992 | Harde et al. | 544/216 |
| 5,098,465 | 3/1992 | Krüger et al. | 544/216 |

OTHER PUBLICATIONS

U.S. patent application Ser. No. 07/795,577, filed Oct. 21, 1991.
"Palmer" in The Structure And Reactions of Heterocyclic Compounds-1967 pp. 98, 99 Edward Arnold (Publishing) Ltd., London.
Alsaidi et al., Synthesis, pp. 921-923 1980.
"Antifungal Drugs", Edited by V. St.Georgiev, Annals of N.Y. Acad. Sci., vol. 544, p. 103, 1988.
"S-Triazines And Derivatives", Interscience Publishers, p. 19, 1959.

*Primary Examiner*—Mukund J. Shah
*Assistant Examiner*—Pavanaram K. Sripada
*Attorney, Agent, or Firm*—William H. Pittman

[57] ABSTRACT

Disubstituted monochlorotriazines such as 2-chloro-4-mesitoxy-6-glycidoxy-1,3,5-triazine are prepared in organic solution by first combining a monoorganoxy dichlorotriazine with an aqueous alkali metal hydroxide solution in a specific concentration and molar ratio, and adding to the mixture thus produced a hydroxyaliphatic or hydroxyaromatic compound, preferably glycidol, in the presence of at least one hydrophilic phase transfer catalyst such as tetra-n-butylammonium bromide. The reaction can be integrated with either or both of a prior step of dichlorotriazine preparation and a subsequent step of capping a hydroxy-terminated polymer, especially a polyphenylene ether.

16 Claims, 1 Drawing Sheet

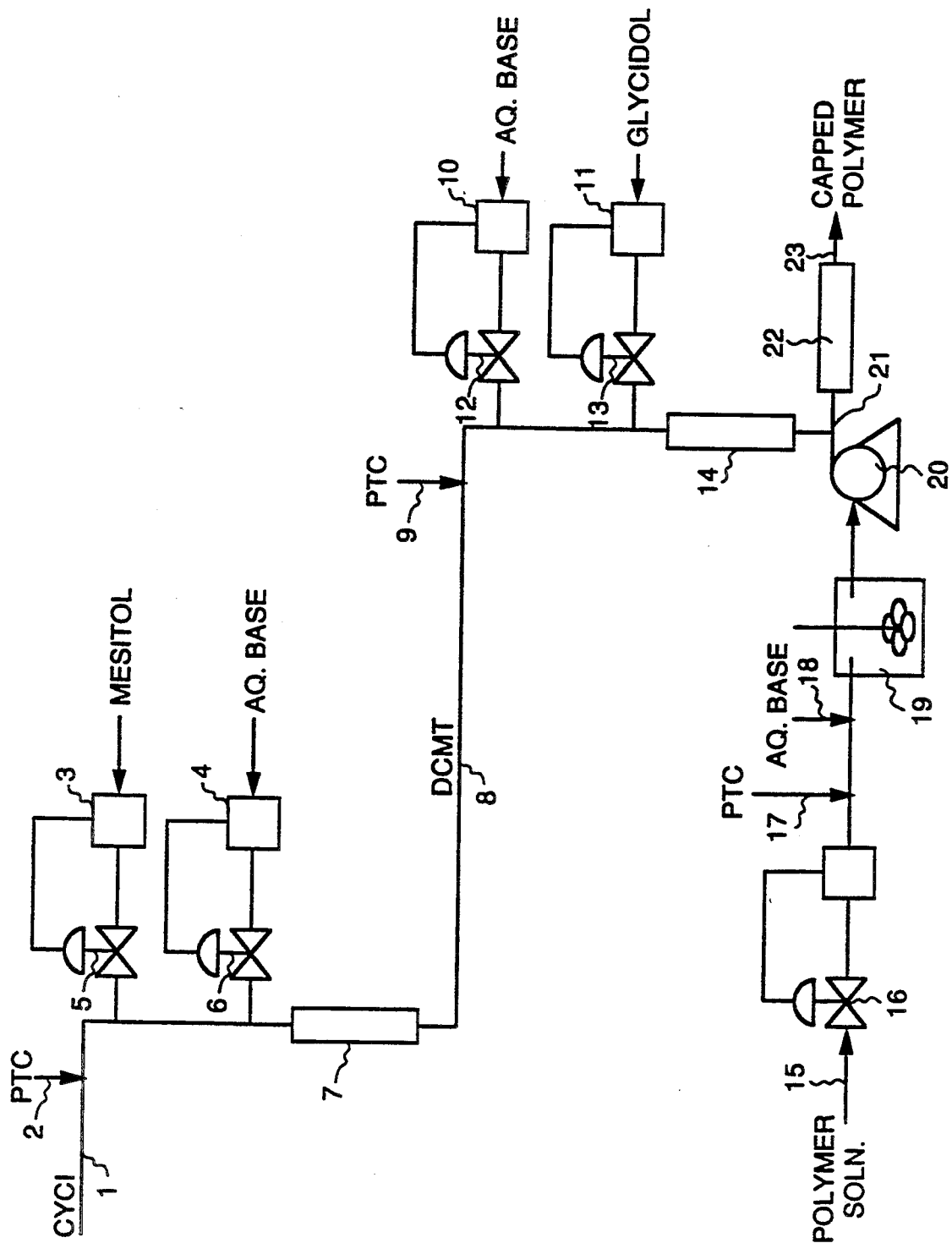

METHOD FOR PREPARING DISUBSTITUTED MONOCHLOROTRIAZINES

This application is a continuation of copending application Ser. No. 08/117,384, filed Sep. 7, 1993, which in turn is a continuation of application Ser. No. 07/957,111, filed Oct. 7, 1992 now abandoned.

This invention relates to the preparation of disubstituted monochlorotriazines, and more particularly to an improved method for their preparation which can be integrated in an overall scheme for capping polymers.

In recent years, monochlorotriazines containing two different substituents have become of increasing interest by reason of their capability of reaction with hydroxy-terminated polymers to form functionalized polymers, which in turn can be converted to copolymers. For example, U.S. Pat. No 4,895,945 describes the preparation of such compounds as 2-chloro-4-butoxy-6-glycidoxy-1,3,5-triazine and its analog wherein the butyl group is replaced by a mesityl group, and the use of such compounds as capping agents for polyphenylene ethers. Similar triazines containing a chloro- or phosphatoalkyl group are disclosed in copending, commonly owned application Ser. No. 07/654,444 U.S. Pat. No. 5,159,075.

Monochlorotriazines of this type are typically prepared by the reaction of a monoalkyl- or monoaryldichlorotriazine with an aliphatic or aromatic monohydroxy compound, most often containing another reactive functional group, under alkaline conditions. The aforementioned patent and application disclose specific methods in which the dichlorotriazine and hydroxy compound are brought into contact in a substantially non-polar organic solvent, and an aqueous alkali metal hydroxide solution is subsequently introduced.

A further method of this type is disclosed in copending, commonly owned application Ser. No. 07/795,577. In that method, a phase transfer catalyst is employed and the reagents are brought into contact only after water and inorganic salts formed in previous reactions (e.g., preparation of the dichlorotriazine) have been removed. By the use of this method, it is often possible to substantially decrease the proportion of hydroxy compound needed to produce the monochlorotriazine in high yield.

A problem which has been encountered in the use of these methods for monochlorotriazine production is that the product may undergo slow decomposition unless it is isolated from the organic solution in which it is prepared. It has been found, for example, that 2-chloro-4-mesitoxy-6-glycidoxy-1,3,5-triazine (hereinafter sometimes "MGCC") prepared as described in Ser. No. 07/795,577, when stored as a 0.5M solution in the toluene in which it was prepared, decomposes at the rate of about 16% per month. A similar 1M solution decomposes at 23% per month. Under accelerated conditions in refluxing toluene, the molarity of the latter solution dropped from 1.0 to about 0.13 in less than 200 minutes.

This tendency to decompose can be suppressed, as previously noted, by isolating the product; e.g., by precipitation by addition of a non-solvent, filtration and redissolution. When this is done, a 1M solution of MGCC in refluxing toluene retains its full strength for at least 3 hours. However, such operations are inconvenient and, on a commercial scale, frequently impractical.

It is of interest, therefore, to develop methods for preparing disubstituted monochlorotriazines which have very long shelf lives when stored in solution in the solvent in which they were prepared. It is also of interest to develop a method which may be performed under either batch or continuous conditions, and which, when desired, can be integrated with a preceding dichlorotriazine-forming step and with a subsequent step of capping a hydroxy-terminated polymer. These goals are achieved by the present invention.

Accordingly, the, invention is a method for preparing a disubstituted monochlorotriazine (hereinafter sometimes simply "monochlorotriazine") which comprises contacting (A) a monoorganoxy dichlorotriazine in solution in (B) a substantially non-polar organic solvent with (C) at least one aqueous alkali metal hydroxide solution having a concentration in the range of about 20–50% by weight based on total aqueous solution, the molar ratio of alkali metal hydroxide to total triazine moieties being in the range of about 1.0–2.0:1; and adding to the mixture thus produced, at a temperature in the range of about 0°–35° C., (D) a hydroxyaliphatic or hydroxyaromatic compound in the presence of (E) at least one hydrophilic phase transfer catalyst, the molar ratio of reagent D to total triazine moieties being in the range of about 1.0–1.8:1.

The drawing is a flow diagram of one aspect of the invention.

Reagent A in the method of this invention is a monoorganoxy dichlorotriazine (hereinafter sometimes simply "dichlorotriazine"). As used herein, the term "organoxy" refers to an organic substituent bound via an oxygen atom to the triazine ring.

While any triazine isomer may be employed, the 1,3,5-triazines are preferred. The organoxy group thereon is most often an alkoxy or aryloxy group which may be unsubstituted or substituted. Any substituents should be non-reactive under conditions of monochlorotriazine preparation, polymer capping and copolymer formation. Alkyl radicals having about 2–10 carbon atoms and aromatic radicals having about 6–10 carbon atoms are especially preferred.

Illustrative alkoxy radicals are ethoxy, 1-propoxy, 2-propoxy, 1-butoxy and 1-hexoxy. Illustrative aryloxy radicals are phenoxy, 2,6-xylenoxy, mesitoxy (i.e., 2,4,6-trimethylphenoxy) and 1-naphthoxy. Most preferred are the aryloxy radicals, especially phenoxy, 2,6-xylenoxy and mesitoxy.

Reagent B is a substantially non-polar organic solvent. The preferred solvents are substantially water-immiscible liquids such as chloroform, methylene chloride, toluene, xylene and chlorobenzene. Aromatic liquids are especially preferred, with aromatic hydrocarbons and especially toluene being most preferred.

Reagent C is an aqueous alkali metal hydroxide solution (hereinafter sometimes "base solution"). The preferred alkali metal hydroxides are sodium hydroxide and potassium hydroxide, with sodium hydroxide being especially preferred because of its availability and effectiveness. Its concentration is in the range of about 20–50% and preferably about 20–40%.

Reagent D is a hydroxyaliphatic or hydroxyaromatic compound, preferably a monohydroxy compound, usually containing about 2–20 carbon atoms. It may be free from non-hydrocarbon substitutents, as illustrated by phenol, whereupon the synthesized monochlorotriazine, upon reaction with a hydroxy-terminated polymer, forms a diaryloxytriazine-capped polymer which may undergo a displacement reaction with such polymers as polyamides to form a copolymer.

The preferred compounds for use as reagent D, however, are hydroxyaliphatic compounds containing substituents which can undergo addition or substitution reactions with nucleophilic polymers such as polyesters and polyamides. Illustrative substituents of this type are epoxy, halide and phosphate groups. Suitable groups, and the chlorotriazines prepared therefrom, are disclosed in the aforementioned U.S. Pat. No. 4,895,945 and copending application Ser. No. 078/654,444, the disclosures of which are incorporated by reference herein. Especially preferred are glycidol, 2-diethylphosphatoethanol and 2-di-n-butylphosphatoethanol.

Reagent E is at least one phase transfer catalyst. Phase transfer catalysts are believed to function by facilitating transfer of a reagent which is normally substantially insoluble in the aqueous or organic phase of a heterogeneous reaction mixture across the phase interface into said phase.

The phase transfer catalysts used according to the invention are the hydrophilic catalysts. By "hydrophilic" is meant one which is predominantly soluble in and compatible with the aqueous phase. Tetraalkylammonium and tetraalkylphosphonium salts (e.g., halides, bisulfates) free from aromatic substituents and characterized by the presence of alkyl groups containing up to about 5 carbon atoms and the absence of larger alkyl groups are especially preferred. Examples of such compounds are tetra-n-butylammonium bromide, chloride and bisulfate and the corresponding phosphonium salts.

In the present invention, the dichlorotriazine is first dissolved in the organic solvent. The concentration of the solution thus prepared is typically about 15-30% by weight.

It is often preferred to employ a dichlorotriazine which has been prepared by the method disclosed in copending, commonly owned application Ser. No. 07/946,115, by the reaction of cyanuric chloride with at least one monohydroxyaromatic compound in the presence of an organic solvent, a specifically defined phase transfer catalyst and a base solution having a concentration in the range of about 1-20% by weight. By reason of the substantially higher base concentration required according to the present invention, it is generally not feasible to employ dichlorotriazine in the mixture in which it was originally prepared. Separation of said product, at least from the aqueous phase, is required. If a hydrophilic phase transfer catalyst was employed in the preparation of the dichlorotriazine, it will be lost in the course of such separation and the addition of further phase transfer catalyst will thus be necessary.

Aqueous base (reagent C) with a concentration in the range of about 20-50%, preferably about 25-45%, is brought into contact with the dichlorotriazine. The amount of aqueous base employed is calculated to provide a molar ratio of base to total triazine moieties in the range of about 1.0-2.0:1 and preferably 1.1-1.8:1.

At this point, a word is in order about the calculation of molar ratios for the purposes of this invention. It is frequently convenient to prepare dichlorotriazine from cyanuric chloride immediately before conversion of the former to monochlorotriazine, and somewhat burdensome to analyze the monochlorotriazine-containing product mixture prior to said conversion. The yield of dichlorotriazine from cyanuric chloride is usually very high, often approaching 100%. Therefore, it is assumed herein that conversion of cyanuric chloride to dichlorotriazine has been complete. In order to avoid ambiguity, however, molar ratios and mole percentages herein are based on total triazine moieties in the material being analyzed. Since all triazine moieties can be considered as having originated in cyanuric chloride, this is essentially equivalent to calculating such ratios on the basis of the amount of cyanuric chloride originally employed for dichlorotriazine preparation.

Reagent D, the hydroxyaliphatic or hydroxyaromatic compound, is charged to the reaction mixture no earlier than the time at which the aqueous base is charged. It is highly preferred that the phase transfer catalyst also be present at the time reagent D is charged. In other respects, the precise order of reagent addition is not critical. For example, the phase transfer catalyst may be charged prior to, simultaneously with or immediately following the aqueous base. The proportion thereof is an effective amount to catalyze the reaction and is usually about 1-5 mole percent based on total triazine moieties.

Reagent D may be charged simultaneously with or following the charging of aqueous base and phase transfer catalyst. It is generally preferred, however, that the phase transfer catalyst be in contact with reagent A at the time of charging of both aqueous base and reagent D; and still more preferred that it be in a state of intimate blending with the reaction mixture at that time, since reaction time and monochlorotriazine yield are optimized if that is the case. It is usually advantageous, particularly if the reaction is run on a large scale, to introduce the phase transfer catalyst in aqueous solution rather than as a solid.

The molar ratio of reagent D to total triazine moieties is in the range of about 1.0-1.8:1. It is most often in excess of 1.0:1 and up to about 1.1:1. Reaction temperatures are in the range of about 0°-35° C. and preferably about 5°-30° C. Under these conditions, conversion of dichlorotriazine (i.e., the proportion thereof which disappears from the reaction mixture expressed as a percentage of the amount originally charged) is usually at least about 80% and often 90% or greater. Yields of monochlorotriazine, as a percentage of the cyanuric chloride originally employed in the preparation of reagent A, are usually at least about 55% and often greater than 70%.

The method of this invention may be employed either batchwise or continuously. In continuous operation, a stream of dichlorotriazine solution may be charged with aqueous base and phase transfer catalyst (the latter also preferably in aqueous solution), the order of charging not being critical, and finally with reagent D. It may then be passed to an agitated vessel having sufficient volume to provide the desired residence time, which may be as little as about 30-35 minutes under properly adjusted conditions. In another embodiment, the agitated vessel is replaced by a suitable static mixer or the like, with stream velocity adjusted to provide the necessary residence time.

The combined stream can then pass to a holding vessel in which separation of aqueous and organic phases occurs. The organic phase may be recovered, and subjected to a chlorotriazine isolation operation if desired. However, isolation is not generally necessary.

A further embodiment includes an integrated prior step of dichlorotriazine preparation from cyanuric chloride and a suitable monohydroxy compound, typically a monohydroxyaromatic compound. The conditions of the dichlorotriazine preparation may preferably be those disclosed in the aforementioned copending application Ser. No. 07/946,115. For this purpose, cyanuric chloride, monohydroxyaromatic compound, phase transfer catalyst and organic solvent may be combined and continuously brought into contact with aqueous base. Residence times as short as 30 seconds, and typically on the order of 30–300 seconds, are usually satisfactory for dichlorotriazine preparation. After phase separation in a holding vessel similar to that previously described, the organic phase may be combined with further phase transfer catalyst, aqueous base and reagent D as described hereinabove.

A still further embodiment involves integration with a subsequent step of polymer capping, and especially preparation of capped polymer from cyanuric chloride in a single operation. In this embodiment, monochlorotriazine solution produced as described hereinabove is further contacted with a stream of hydroxy-terminated polymer solution and further organic solvent, which solution has previously been combined with aqueous base and, optionally, phase transfer catalyst to form a salt of the hydroxy-terminated polymer. As described in copending, commonly owned application Ser. No. 07/772,176, now abandoned the capping step when employed for the treatment of such polymers as polyphenylene ethers can be completed in times as short as 30 seconds. Following completion of the capping reaction, the polymer solution may be devolatilized by known methods, which may include extruder devolatilization aided by a non-solvent as described in U.S. Pat. No. 5,043,421.

BRIEF DESCRIPTION OF THE DRAWINGS

Reference is now made to the drawing, which is a flow chart of an exemplary completely integrated process of the present invention for conversion of cyanuric chloride to capped polymer. Cyanuric chloride (CYCl) dissolved in a suitable solvent, preferably toluene, is introduced into the system via line 1, and phase transfer catalyst (PTC) is added at 2. Mesitol and aqueous base are added from vessels 3 and 4, the rates of addition being controlled by valves 5 and 6 respectively. The reactant mixture then passes into static mixer 7, the residence time therein being effective to produce a toluene solution of the desired 2,4-dichloro-6-mesitoxy-1,3,5-triazine (DCMT).

The DCMT solution may be separated from the aqueous phase (separation equipment not shown). It then passes through line 8 and is charged with hydrophilic phase transfer catalyst at 9. The resulting mixture is then contacted with aqueous base and glycidol from vessels 10 and 11, their addition rates being regulated by valves 12 and 13 respectively. The mixture passes into a second static mixer 14, wherein it is converted to MGCC.

Polymer (typically polyphenylene ether) solution is introduced at 15, the introduction rate being regulated by valve 16. Phase transfer catalyst and aqueous base are respectively added at 17 and 18, and the mixture passes into continuous stirred tank reactor 19 where it is agitated for a time sufficient to convert the polymer to its salt, typically the sodium salt. It is then pumped via pump 20 to contact point 21 with the MGCC solution, and thence into a third static mixer 22 where conversion to capped polymer takes place. The capped polymer solution is removed at 23.

The method of this invention is illustrated by the following examples. All parts and percentages are by weight. The dichlorotriazine employed was 2,4-dichloro-6-mesitoxy-1,3,5-triazine in the form of a toluene solution prepared by the reaction of 14 grams (75.9 mmol.) of cyanuric chloride with 10.42 grams (76.5 mmol.) of mesitol in 86 grams of toluene, in the presence of 151.8 mmol. of sodium hydroxide as an aqueous solution, 1.52 mmol. of tetra-n-butylammonium bromide and 1 gram of naphthalene as an internal standard.

Yield percentages in the examples are based on cyanuric chloride. As used herein, "yield" is the number of moles of product as a percentage of the number of moles of reactant, and "conversion" is the number of moles of reactant consumed as a percentage of that originally present.

EXAMPLES 1–8

Portions of dichlorotriazine solution in a 400-ml. beaker were stirred with a magnetic stirrer and various quantities of tetra-n-butylammonium bromide were added. The solution was cooled to 5°–10° C. in an ice-water bath (ice-salt-water in Example 8) and various quantities of aqueous sodium hydroxide solution were added, followed immediately by 4.8 grams (83.5 mmol.) of glycidol, whereupon an exotherm was noted. A timer was started when the glycidol was added and the temperatures of the reaction mixtures were monitored as the reaction proceeded. Aliquots were periodically removed, quenched by addition to carbon dioxide-saturated water and analyzed by liquid chromatography. The percentage conversion of dichlorotriazine and the yield of MGCC were determined for each aliquot.

The results are given in the following table, in comparison with two controls: Control 1 in which no phase transfer catalyst was employed, and Control 2 in which the phase transfer catalyst was a methyltrialkylammonium bromide in which the alkyl groups contained 8–10 carbon atoms, an organophilic catalyst. Mole ratios and mole percents in the table are based on cyanuric chloride.

|  | Example | | | | | | | | Control | Control |
| --- | --- | --- | --- | --- | --- | --- | --- | --- | --- | --- |
|  | 1 | 2 | 3 | 4 | 5 | 6 | 7 | 8 | 1 | 2 |
| Phase transfer cat., mole % | 2 | 2 | 2 | 4 | 2 | 2 | 2 | 2 | 0 | 2 |
| Aqueous base: | | | | | | | | | | |
| Concentration, % | 50 | 40 | 30 | 30 | 30 | 30 | 30 | 30 | 30 | 50 |
| Mole ratio | 1.0:1 | 1.8:1 | 1.8:1 | 1.8:1 | 1.6:1 | 1.4:1 | 1.2:1 | 1.4:1 | 1.8:1 | 1.0:1 |
| Temperature, °C.[1] | 7–24 | 6–30 | 12–22 | 9–26 | 7–20 | 11–20 | 9–21 | (1)–7 | 10–14 | 6–24 |
| Time to max. temp., sec. | 60 | 60 | 120 | 60 | 120 | 40 | 120 | 360 | 30 | 120 |
| Final analysis time, min. | 188 | 110 | 62 | 61 | 62 | 122 | 91 | 120 | 230 | 185 |
| Dichlorotriazine conv., % | 80 | 95 | 98 | 100 | 97 | 96 | 95 | 98 | 70 | 95 |

| | Example | | | | | | | | Control | Control |
|---|---|---|---|---|---|---|---|---|---|---|
| | 1 | 2 | 3 | 4 | 5 | 6 | 7 | 8 | 1 | 2 |
| MGCC yield, % | 55 | 65 | 73 | 81 | 72 | 73 | 72 | 68 | 38 | 67[2] |

[1]Negative value in parentheses.
[2]Heavy emulsion formation; separated by centrifugation.

A comparison of Example 1 with Control 2 shows that emulsion formation was substantially greater with the use of an organophilic than a hydrophilic phase transfer catalyst. The substantial deterioration in yield when no phase transfer catalyst was employed is demonstrated by a comparison of Control 1 with Example 4.

A comparison of Examples 1–4 with Examples 5–8 shows that there is a trend toward increased conversion and yield with base concentrations within the preferred ranges. Similarly, comparison of Examples 6 and 8 shows an increase in yield upon operating within the preferred temperature range.

What is claimed is:

1. A method for preparing a disubstituted monochlorotriazine which comprises contacting (A) a monoorganoxy dichloro-1,3,5-triazine wherein the organoxy group is an alkyl radical having about 2–10 carbon atoms or an aromatic radical having about 6–10 carbon atoms in solution in (B) a substantially non-polar organic solvent with (C) at least one aqueous alkali metal hydroxide solution having a concentration in the range of about 20–50% by weight based on total aqueous solution, the molar ratio of alkali metal hydroxide to total triazine moieties being in the range of about 1.0–2.0:1; and adding to the mixture thus produced, at a temperature in the range of about 0°–35° C., (D) a monohydroxyaliphatic compound containing about 2–20 carbon atoms in the presence of (E) at least one hydrophilic phase transfer catalyst, the molar ratio of reagent D to total triazine moieties being in the range of about 1.0–1.8:1, and the proportion of phase transfer catalyst being about 1.0–1.8:1 and them proportion of phase transfer catalyst being about 1–5 mole percent based on total triazine moieties.

2. A method according to claim 1 wherein the dichlorotriazine is 2,4-dichloro-6-mesitoxy-1,3,5-triazine.

3. A method according to claim 2 wherein the molar ratio of reagent D to total triazine moieties is in excess of 1.0:1 and up to about 1.1:1.

4. A method according to claim 2 wherein reagent D contains a substituent which can undergo an addition or substitution reaction with a nucleophilic polymer.

5. A method according to claim 4 wherein reagent D is glycidol.

6. A method according to claim 4 wherein reagent D is 2-diethylphosphatoethanol or 2-di-n-butylphosphatoethanol.

7. A method according to claim 1 wherein the phase transfer catalyst is a tetraalkylammonium or tetraalkylphosphonium salt characterized by the presence of alkyl groups containing up to about 5 carbon atoms and the absence of larger alkyl groups.

8. A method according to claim 7 wherein the phase transfer catalyst is introduced in aqueous solution.

9. A method according to claim 7 wherein the phase transfer catalyst is tetra-n-butylammonium bromide.

10. A method according to claim 1 wherein the solvent is toluene.

11. A method according to claim 1 wherein the alkali metal hydroxide is sodium hydroxide.

12. A method according to claim 1 wherein the concentration of the alkali metal hydroxide solution is in the range of about 25–45%.

13. A method according to claim 1 wherein the temperature is in the range of about 5°–30° C.

14. A method according to claim 1 wherein the reaction is conducted batchwise.

15. A method according to claim 1 wherein the reaction is conducted continuously.

16. A method according to claim 15 wherein the reaction is integrated with a prior step of dichlorotriazine preparation from cyanuric chloride and a monohydroxy compound.

* * * * *